US012400753B2

(12) United States Patent
Liu et al.

(10) Patent No.: US 12,400,753 B2
(45) Date of Patent: Aug. 26, 2025

(54) COLLABORATIVE FEATURE ENSEMBLING ADAPTATION FOR DOMAIN ADAPTATION IN UNSUPERVISED OPTIC DISC AND CUP SEGMENTATION

(71) Applicant: University of Florida Research Foundation, Inc., Gainesville, FL (US)

(72) Inventors: Peng Liu, Gainesville, FL (US); Ruogu Fang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 517 days.

(21) Appl. No.: 17/915,362

(22) PCT Filed: Mar. 23, 2021

(86) PCT No.: PCT/US2021/023678
§ 371 (c)(1),
(2) Date: Sep. 28, 2022

(87) PCT Pub. No.: WO2021/202170
PCT Pub. Date: Oct. 7, 2021

(65) Prior Publication Data
US 2023/0141896 A1 May 11, 2023

Related U.S. Application Data

(60) Provisional application No. 63/001,771, filed on Mar. 30, 2020.

(51) Int. Cl.
*A61B 3/00* (2006.01)
*A61B 3/12* (2006.01)
(Continued)

(52) U.S. Cl.
CPC .......... *G16H 30/40* (2018.01); *A61B 3/0025* (2013.01); *A61B 3/12* (2013.01); *G06V 10/82* (2022.01); *G06V 40/197* (2022.01)

(58) Field of Classification Search
CPC ...... G16H 30/40; G06V 40/197; G06V 10/82; A61B 3/0025; A61B 3/12
(Continued)

(56) References Cited

U.S. PATENT DOCUMENTS 11,295,178 B2 * 4/2022 Peng ..................... G06V 10/32
2011/0091083 A1 4/2011 Liu et al.
(Continued)

OTHER PUBLICATIONS

Peng Liu et al. "CFEA: Collaborative Feature Ensembling Adaptation for Domain Adaptation in Unsupervised Optic Disc and Cup Segmentation". The 22nd International Conference on Medical Image Computing and Computer Assisted Intervention. <https://arxiv.org/abs/1910.07638>. 9 pages. Oct. 16, 2019.
(Continued)

*Primary Examiner* — Allen H Nguyen
(74) *Attorney, Agent, or Firm* — Thomas | Horstemeyer, LLP

(57) ABSTRACT

Embodiments of the present disclosure are directed to training a neural network for ocular cup (OC) or ocular disc (OD) detection. One such method comprises initiating training of a first network to learn detection of OC/OD regions within a labeled source sample from a source domain; sharing training weights of the first network with a second network; initiating training of the second network to learn detection of OC/OD regions within an unlabeled sample from a target domain; transferring average training weights of the second network to a third network; initiating training of the third network to learn detection of OC/OD regions within an unlabeled sample from the target domain; computing a mean square error loss between the third network and the second network for a same target sample; and adjusting training weights of the second network based on the mean square error loss computation.

20 Claims, 11 Drawing Sheets

(51) Int. Cl.
　　　*G06V 10/82*　　　(2022.01)
　　　*G06V 40/18*　　　(2022.01)
　　　*G16H 30/40*　　　(2018.01)

(58) Field of Classification Search
　　　USPC .......................................................... 382/128
　　　See application file for complete search history.

(56) References Cited

U.S. PATENT DOCUMENTS

| | | | | |
|---|---|---|---|---|
| 2015/0363930 | A1* | 12/2015 | Xu | G06F 18/22 |
| | | | | 382/128 |
| 2016/0092721 | A1* | 3/2016 | Kanagasingam | G06V 40/193 |
| | | | | 348/78 |
| 2016/0100806 | A1* | 4/2016 | Mwanza | A61B 5/7275 |
| | | | | 351/205 |
| 2017/0112372 | A1 | 4/2017 | Chakravorty et al. | |
| 2018/0181833 | A1* | 6/2018 | Yin | G06V 40/193 |

OTHER PUBLICATIONS

Lin Teng et al. "DMCNN: A Deep Multiscale Convolutional Neural Network Model for Medical Image Segmentation". Journal of Healthcare Engineering. <https://www.hindawi.com/journals/jhe/2019/8597606/>/ pp. 1-10. Dec. 2019.

Weichen Zhang et al. "Colloborative and Adversarial Network for Unsupervised Domain Adaptation". Proceedings of the IEEE Conference on Computer Vision and Pattern Recognition (CVPR). <https://openaccess.thecvf.com/content_cvpr_2018/html/Zhang_Collaborative_and_Adversarial_CVPR_2018_paper.html>. pp. 3801-3809. Dec. 17, 2018.

International Search Report and Written Opinion for International Application No. PCT/US2021/023678 mailed Jun. 25, 2021.

\* cited by examiner (a) Zeiss Visucam 500  (b) Canon CR-2

Algorithm 1 Training procedure of the proposed framework.

Input: $\mathcal{D}_s, \mathcal{D}_t$ = source and target domain dataset
Input: $f_{\bar{\phi}}, f_\phi$ = source, target domain networks with weights $\bar{\phi}$ and $\phi$, respectively
Input: $f_{\phi'}$ = teacher network with trainable weights $\phi'$
Input: $D_E$ = discriminator network for the encoder
Input: $D_D$ = discriminator network for the decoder ▷ initialize ensemble weights
$\phi'_0 \leftarrow \phi_0$
for $t$ in $[1, num\_iterations]$ do
    randomly sample a minibatch of images $B_s$ from $\mathcal{D}_s$
    randomly sample a minibatch of images $B_t$ from $\mathcal{D}_t$
▷ Calcuate segmentation loss
$l_{seg} \leftarrow \mathcal{L}_{seg}(x_s^{j \in B_s})$
update $\bar{\phi}$ with $l_{seg}$ using, e.g., ADAM
▷ update teacher network with Eq. 3
$\phi'_t \leftarrow \alpha \phi'_{t-1} + (1 - \alpha)\phi_t$
▷ evaluate outputs for source inputs
$p_{sf}^{j \in B_s}, p_{so}^{j \in B_s} \leftarrow f_{\bar{\phi}}(x_s^{j \in B_s})$
▷ evaluate student outputs for target
$p_{tsf}^{j \in B_t}, p_{tso}^{j \in B_t} \leftarrow f_\phi(x_t^{j \in B_t})$
▷ calculate loss with Eq. 4
$l_{adv}^E \leftarrow \mathcal{L}_{adv}^E(x_s^{j \in B_s})$
▷ calculate loss with Eq. 5
$l_{adv}^D \leftarrow \mathcal{L}_{adv}^D(x_s^{j \in B_s})$ Continued at FIG. 2D

FIG. 2C

Continued from FIG. 2C

▷ calculate adversarial loss
$l_{adv} \leftarrow \lambda_{adv}^E l_{adv}^E + \lambda_{adv}^D l_{adv}^D$
update $\phi$ and $\tilde{\phi}$ with $l_{adv}$ using, e.g., ADAM
▷ calculate loss with Eq. 6
$l_{dis}^E \leftarrow \mathcal{L}_d^E(x_s^{j \in B_s}, x_t^{j \in B_t})$
▷ calculate loss with Eq. 7
$l_{dis}^D \leftarrow \mathcal{L}_d^D(x_s^{j \in B_s}, x_t^{j \in B_t})$
update $\mathbf{D}_E$ and $\mathbf{D}_E$ with $l_{dis}^E$ and $l_{dis}^D$ using, e.g., ADAM
$P_{nf}^{j \in B_t}, P_{no}^{j \in B_t} \leftarrow f_{\phi'}(\mathbf{x}_t^{j \in B_t})$
▷ calculate decoder MSE loss with Eq. 8
$l_{mse}^E \leftarrow \mathcal{L}_{mse}^E(x_t^{j \in B_t})$
▷ calculate decoder MSE loss with Eq. 9
$l_{mse}^D \leftarrow \mathcal{L}_{mse}^D(x_t^{j \in B_t})$
▷ calculate adversarial loss
$l_{mse} \leftarrow \lambda_{mse}^E l_{mse}^E + \lambda_{mse}^D l_{mse}^D$
update $\phi$ with $l_{mse}$ using, e.g., ADAM
end for
return $\phi'$

FIG. 2D

COLLABORATIVE FEATURE ENSEMBLING ADAPTATION FOR DOMAIN ADAPTATION IN UNSUPERVISED OPTIC DISC AND CUP SEGMENTATION

CROSS-REFERENCE TO RELATED APPLICATION

This application is the 35 U.S.C. § 371 national stage application of International Application No. PCT/US2021/023678, filed Mar. 23, 2021, which claims priority to co-pending U.S. provisional application entitled, "CFEA: COLLABORATIVE FEATURE ENSEMBLING ADAPTATION FOR DOMAIN ADAPTATION IN UNSUPERVISED OPTIC DISC AND CUP SEGMENTATION," having Ser. No. 63/001,771, filed Mar. 30, 2020, which is entirely incorporated herein by reference.

TECHNICAL FIELD

The present disclosure is generally related to the computerized diagnosis of ocular diseases.

BACKGROUND

Early diagnosis is vital for the treatment of various vision degradation diseases, such as glaucoma, Diabetic Retinopathy (DR), and age-related macular degeneration. Many eye diseases can be revealed by the morphology of Optic Disc (OD) and Optic Cup (OC). For instance, glaucoma is usually characterized by the large Cup to Disc Ratio (CDR), the ratio of the vertical diameter of the cup to the vertical diameter of the disc. Currently, determining CDR is mainly performed by pathology specialists. However, it is extremely expensive to accurately calculate CDR by human experts. Furthermore, manual delineation of these lesions also introduces subjectivity, intra- and intervariability. Therefore, it is essential to automate the process of calculating CDR. OD and OC segmentation are adopted to automatically calculate the CDR. Nevertheless, OD segmentation is challenging because pathological lesions usually occur on OD boundaries, which affect the accurate identification of the OD region. Accurate OC segmentation is more challenging due to the region overlap between the cup and the blood vessels.

Recently, deep learning based methods have been proposed to overcome these challenges and some of them, e.g., M-Net, have demonstrated impressive results. Although these methods tend to perform well when being applied to well-annotated datasets, the segmentation performance of a trained network may degrade severely on datasets with different distributions, particularly for the retinal fundus images captured with different imaging devices (e.g., different cameras, as illustrated in FIG. 1). The variance among the diverse data domains limits deep learning's deployment in reality and impedes us from building a robust application for retinal fundus image parsing. To recover the degraded performance, annotating the fundus images captured from every new domain and then retraining or fine-tuning a model is an easy way but extremely expensive and even impractical for the medical areas that require expertise.

SUMMARY

Embodiments of the present disclosure provide systems, apparatuses, and methods for training a neural network for ocular cup (OC) and/or ocular disc (OD) detection. One such method comprises drawing a mini-batch of labeled source domain samples from a source domain and unlabeled target samples from a target domain for a plurality of training iterations, wherein a domain shift exists between the source domain and the target domain; initiating training of a first network to learn detection of OC and/or OD regions within a labeled source sample from the source domain, wherein training weights of the first network are adapted based on a loss calculated from an output of the first network and a ground truth for a same source sample; sharing training weights of the first network with a second network; initiating training of the second network to learn detection of OC or OD regions within an unlabeled sample from the target domain, wherein training weights of the second network are adapted based on an adversarial loss calculated from an output of the second network and the output of the first network for the same sample across the source and target domains; adjusting the training weights of the first network and the second network based on the calculated adversarial loss; transferring average training weights of the second network to a third network; initiating training of the third network to learn detection of OC and OD regions within an unlabeled sample from the target domain; computing a mean square error loss between an output of the third network and the output of the second network for a same target sample; adjusting the training weights of the second network based on the mean square error loss computation; and/or proceeding with a next iteration of the plurality of training iterations.

The present disclosure can also be viewed as a system for training a neural network for ocular cup (OC) and/or ocular disc (OD) detection. One such system can be comprised of one or more processors and memory storing computer-executable instructions that, when executed by the one or more processors, cause performance of the following operations. Accordingly, the operations can include drawing a mini-batch of labeled source domain samples from a source domain and unlabeled target samples from a target domain for a plurality of training iterations, wherein a domain shift exists between the source domain and the target domain; initiating training of a first network to learn detection of OC or OD regions within a labeled source sample from the source domain, wherein training weights of the first network are adapted based on a loss calculated from an output of the first network and a ground truth for a same source sample; sharing training weights of the first network with a second network; initiating training of the second network to learn detection of OC or OD regions within an unlabeled sample from the target domain, wherein training weights of the second network are adapted based on an adversarial loss calculated from an output of the second network and the output of the first network for the same sample across the source and target domains; adjusting the training weights of the first network and the second network based on the calculated adversarial loss; transferring average training weights of the second network to a third network; initiating training of the third network to learn detection of OC and OD regions within an unlabeled sample from the target domain; computing a mean square error loss between an output of the third network and the output of the second network for a same target sample; adjusting the training weights of the second network based on the mean square error loss computation; and/or proceeding with a next iteration of the plurality of training iterations until each iteration of the plurality of training iterations has been completed.

In one or more aspects for such systems and/or methods, the target and source domains comprise retinal fundal images; the target domain of retinal fundal images is captured from a first retinal fundal camera and the source domain of retinal fundal images is captured from a second retinal fundal camera that is different model camera than the first retinal fundal camera; the first network, the second network, and third network comprise encoder decoder convolutional networks; adversarial losses for domain confusion are added for both encoder and decoder outputs of the first network and the second network; the first, second, and third networks feature multiple discriminators in a plurality of decoder layers; the multiple discriminators comprise 3 or more discriminators; each of the first network, the second network, and the third network comprise a multi-scale input layer, wherein each scale input provides original image information to an encoder layer; and/or the training weights of the third network are an exponential moving average of the training weights of the second network. Additionally, the one or more aspects for such systems and/or methods, an exemplary system/method can perform the operation of determining, by the third network after completion of training, a Cup to Disc Ratio for a retinal fundal image.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 2C-2D show an exemplary training procedure algorithm in accordance with various embodiments of the present disclosure.

DETAILED DESCRIPTION

Figure 1:
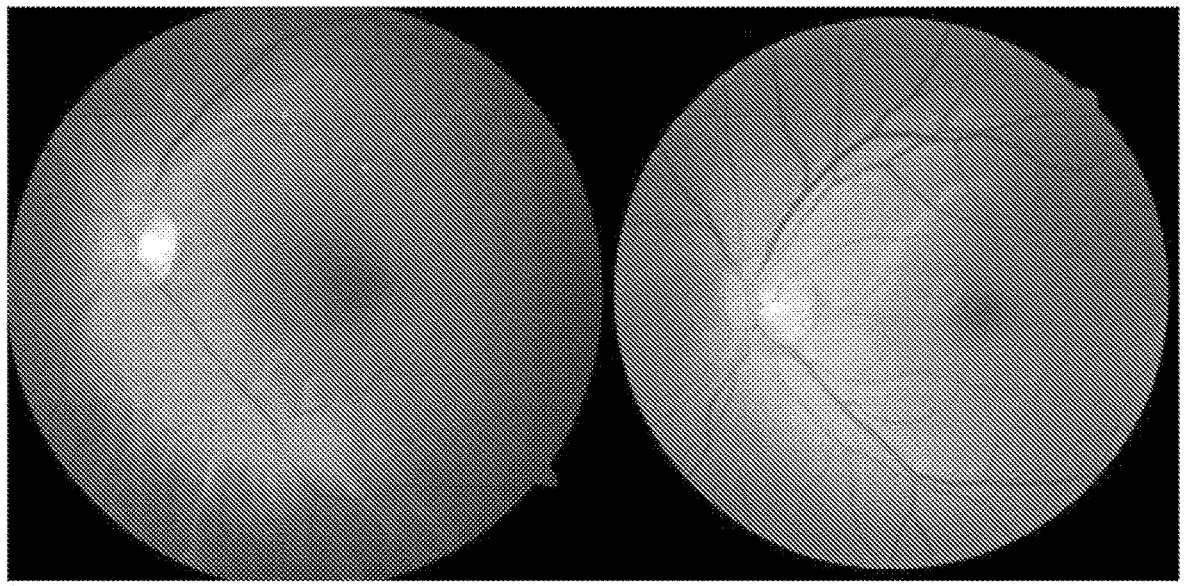
FIG. 1 shows retinal fundus images collected by different fundus cameras in accordance with the present disclosure.

The present disclosure describes various embodiments of systems, apparatuses, and methods for training a neural network for ocular cup (OC) and/or ocular disc (OD) detection. For example, the diversity of retinal imaging devices poses a significant domain shift challenge for deep learning networks, which leads to performance degradation when applying deep learning models to new testing or target domains. Various embodiments in accordance with the present disclosure are directed to an unsupervised domain adaptation framework, referred as Collaborative Feature Ensembling Adaptation (CFEA) or an unsupervised domain adaptation framework, referred as Collaborative Adversarial Domain Adaptation (CADA), to overcome the challenges underlining in a domain shift.

For both CFEA and CADA, the present disclosure takes the advantage of self-ensembling to stabilize the adversarial discriminative learning of latent representations from domain shifting to prevent a neural network (e.g., deep learning network) from getting stuck in a degenerate solution. Most importantly, an unsupervised loss is applied by adversarial learning not only to the output space but also to the input space or the intermediate representations of the network. Thus, from a complementary perspective, adversarial learning can consistently provide various model space and time-dependent weights to self-ensembling to accelerate the learning of domain invariant features and further enhance the stabilization of adversarial learning, forming a benign collaborative circulation and unified framework.

As an overview, the features of the Optic Disc (OD) and Optic Cup (OC) are critical in the diagnosis of eye diseases. For example, ophthalmic pathologies (e.g., glaucoma) can be indicated by the varies of the shape, color, or depth of OD. Besides, the Cup to Disc Ratio (CDR), the ratio of the vertical diameter of the cup to the vertical diameter of the disc, is considered as a valuable feature for diagnosing eye diseases, such as glaucoma, because higher CDR is highly associated with detectable visual field damage. The variance of determining the CDR among professionals is usually significant, which can be caused by both the diversity of retinal fundus images and the different experiences of professionals. Therefore, it is essential to automate the process of calculating CDR. On the one hand, this automated process can reduce the cost of diagnosis. On the other hand, it can stabilize the diagnostic accuracy and improve the efficiency of retinopathy screening procedures.

Image segmentation is a long-term research topic in the field of computer vision and image analysis. It is the basis for feature recognition and quantitative feature analysis. In medical imaging, image segmentation is particularly important since it can help locate related lesions/tumors and provide quantitatively analytical results of shapes/morphologies for clinicians. For example, image segmentation can automatically detect the OD and OC regions and calculate the CDR simultaneously. The OD segmentation can detect the region between retinal and the rim. The challenge to OD detection is pathological lesions usually occurring on the OD boundaries which can affect the accuracy in identifying the OD region. An accurate OC segmentation is more challenging due to the region overlap between the cup and the blood vessels and the color intensity changing between the cup and rim. It is critical to erase these challenges for reducing the incorrect OD and OC segmentation that may cause a false diagnosis.

To tackle this challenge, recent studies have demonstrated the effectiveness of using deep learning for unsupervised domain adaptation to enhance the performance of applying models on unlabeled target domain data. Existing works have mainly focused on minimizing the distance between the source and target domains to align the latent feature distributions of the different domains. Several primary approaches can guide the alignment process, which include image-to-image translation of the input images, adversarial training for the intermediate representations in the layers of the model (encoder or decoder), and applying adversarial learning to the output of the model. However, adversarial discriminative learning usually suffers from the instability of its training. Numerous methods have been studied to tackle this challenge. Self-ensembling is one of them recently applied to visual domain adaptation. In particular, gradient descent is used to train the student, and the exponential moving average of the weights of the student is transferred to the teacher after applying each training sample. The mean square difference between the outputs of the student and the teacher is used as the unsupervised loss to train the student network.

In general, there are several steps to achieve a decent result in detection of OD and OC. Firstly, a pre-trained disc center localization method is used to detect the OD and OC. The localization mainly performs as an attention mechanism so that the network can focus on essential regions and meanwhile, the polar transformation amplifies the relevant features to enable a more accessible learning process. Secondly, the localized areas are transformed (e.g., cropped, re-size, and image coordinate system consistency) into a segmentation model training stage. Lastly, these transformed image regions are fed into an encoder-decoder convolutional network to predict the actual OD and OC regions for arbitrary fundus image. The encoder is performed to extract rich image features; the decoder part is used to produce accurate segmentation results based on the encoded features. These combined techniques can reduce the negative effect on model performance caused by the variance in retinal images. However, the variation is only constrained within one image domain, in which the training and testing images usually have similar distributions, such as background color and intensity. In practice, the testing images can be acquired from different types of cameras and have a varying background or image intensity (as illustrated in FIG. 1). The performance of a model trained on the dataset collected from one domain is severely degraded in another domain. This issue is referred to as "domain shift." It is critical to overcome this issue for a generalized and robust model in medical practice.

Saenko et al. (2010) originally introduced the unsupervised domain adaptation problem in tackling the performance degradation caused by the domain shift. See Saenko, K., Kulis, B., Fritz, M., Darrell, T., "Adapting Visual Category Models to New Domains, European Conference on Computer Vision (ECCV), Springer. pp. 213-226 (2010). In particular, unsupervised domain adaptation aims to tackle a domain shift via adapting the training process of a model in an unsupervised behavior, such that the model is adapted to have a decent performance on the target domain. More importantly, leveraging unsupervised learning can reduce the tremendous and expensive data labeling work for the target domain. Therefore, unsupervised domain adaptation is a promising study for solving the domain shift problems, especially, in the medical field where the data usually is multiple-modality and the data labeling is expensive and requires expertise skills.

Many deep learning-based domain adaptation methods have also recently been proposed and have achieved many encouraging results. Many of these methods tackle the domain shift issue by extracting invariant features across the source and target domains. A critical approach for reducing the domain discrepancy is adversarial learning, which has become a fundamental method to obtain invariant information across multiple domains. In particular, it leverages the gradient discrepancy between learning the labeled and unlabeled data to minimize performance degradation. The implementation can either be image-to-image translation in a convolutional neural network (CNN) input-end or multiple adversarial learning applied at the output-end of a CNN. Noticeably, the image-to-image translation usually introduces artifacts, which may be not a proper approach in the medical field. Therefore, a focus of the present disclosure is on gradient-based adversarial learning.

Although adversarial learning can align the latent feature distribution of the source and target domain and have achieved encouraging results, the results of multiple adversarial learning-based methods easily suffer from sub-optimal performance due to the difficulty of stabilizing the training process of multiple adversarial modules. Thus, in the present disclosure, the Exponential Moving Average (EMA) computing method is leveraged to dynamically ensemble learning weights as embedding multiple adversarial modules in a network. Meanwhile, this stabilization can bring not only a more robust model but also an accurate model to effectively overcome the domain shift issue in the fundus image segmentation problem.

Turning now to a discussion of the problem at issue, unsupervised domain adaptation typically refers to the following scenario: given a labeled source domain dataset with distribution $P(X_s)$ and the corresponding label $Y_s$ with distribution $P(Y_s|X_s)$, as well as a target dataset with distribution $P(X_t)$ and unknown label with distribution $P(Y_t|X_t)$, where $P(X_s) \neq P(X_t)$, the goal is to train a model from both labeled data $X_s$ and unlabeled data $X_t$, with which the expected model distribution $P(\hat{Y}_t|X_t)$ is close to $P(Y_t|X_t)$.

Figure 2A:
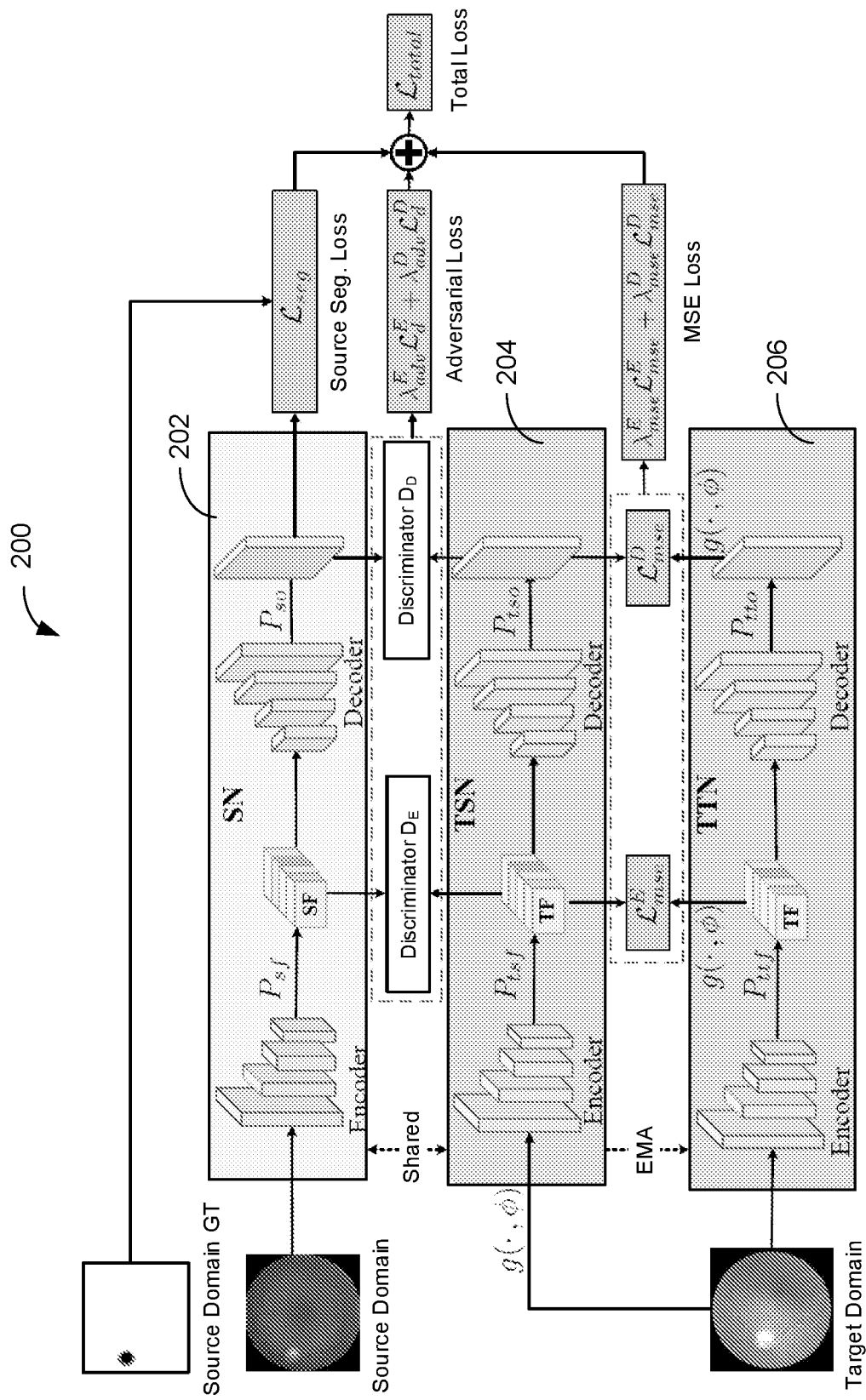
FIG. 2A shows an overview of an exemplary model architecture for Collaborative Feature Ensembling Adaptation (CFEA) in accordance with various embodiments of the present disclosure.

As illustrated in FIG. 2A, an exemplary framework 200 for Collaborative Feature Ensembling Adaptation (CFEA) includes three networks, i.e., the Source domain Network ("first network") (SN, indicated by reference character 202), the Target domain Student Network ("second network") (TSN, indicated by reference character 204) and the Target domain Teacher Network ("third network") (TTN, indicated by reference character 206). Although each of the three networks plays a distinctive role in guiding neural networks to learn domain invariant representations, all of them can interact with each other, benefit from one another, and work collaboratively as a unified framework during an end-to-end training process. SN and TSN focus on supervised learning for labeled samples from the source domain ($X_s$) and adversarial discriminative learning for unlabeled samples from the target domain ($X_t$), separately. More importantly, SN and TSN share the weights that are sequentially learned from both labeled and unlabeled samples. The labeled samples enable the network to learn accurate segmentation predictions while the unlabeled ones bring unsupervised learning and further present a type of perturbation to regularize the model training. Furthermore, TTN conducts the weight self-ensembling part by replicating the average weights of the TSN instead of predictions. TTN solely takes unlabeled target images as input and then the mean square difference between TSN and TTN is computed for the same target sample. Different data augmentations (e.g., adding Gaussian noise and random intensity or brightness scaling) are applied to TSN and TTN to avoid loss vanishing issue.

Figure 2B:
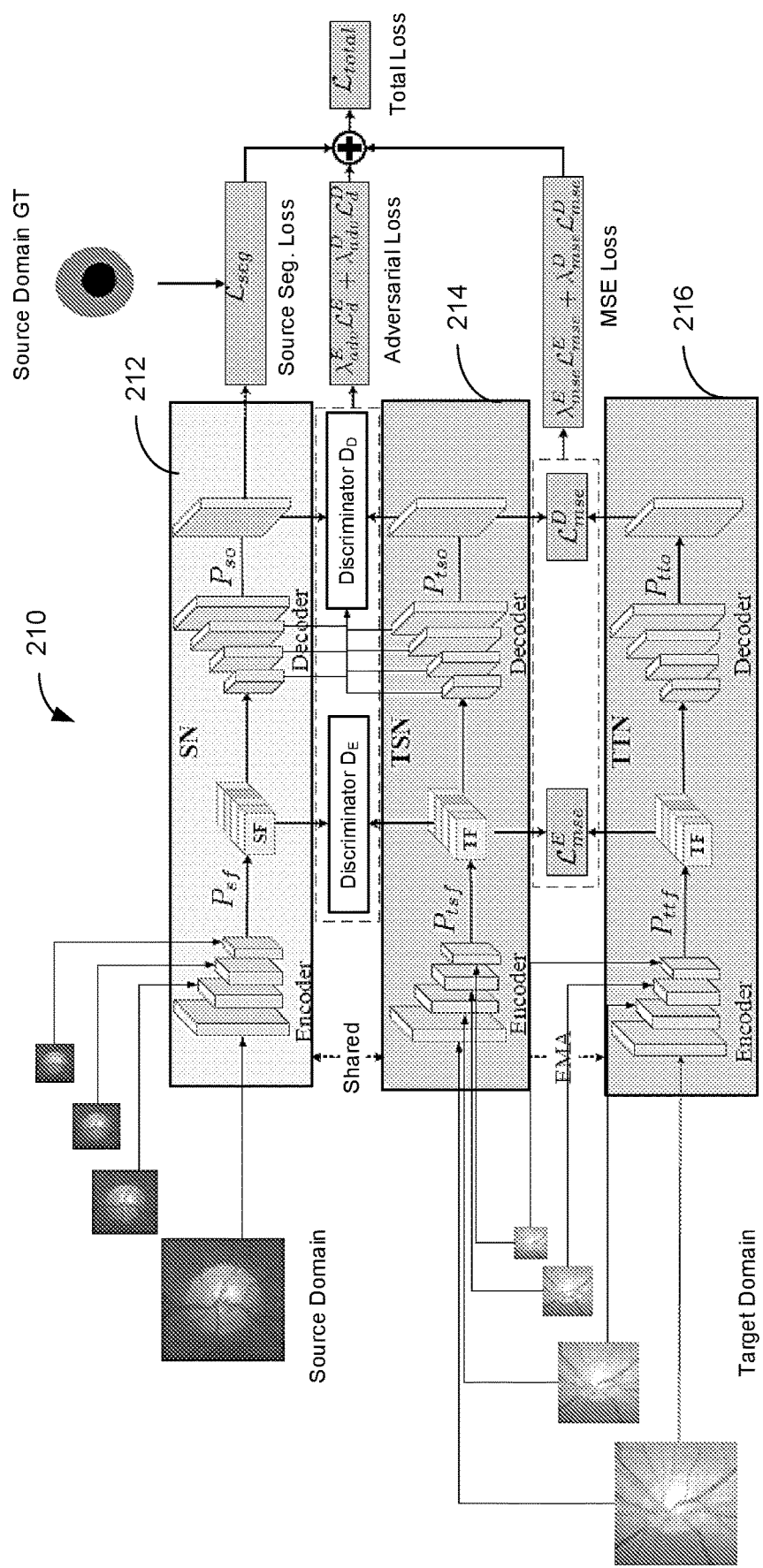
FIG. 2B shows an overview of an exemplary model architecture for Collaborative Adversarial Domain Adaptation (CADA) in accordance with various embodiments of the present disclosure.

As illustrated in FIG. 2B, an exemplary framework 210 for Collaborative Adversarial Domain Adaptation (CADA) mainly includes three networks, i.e., the Source domain Network ("first network") (SN, indicated by reference character 212), the Target domain Student Network ("second network") (TSN, indicated by reference character 214) and the Target domain Teacher Network ("third network") (TTN, indicated by reference character 216). Although each of the three networks plays a distinctive role in guiding networks to learn domain invariant representations, all of them can interact with each other, benefit one another, and work collaboratively as a unified framework during an end-to-end training process. SN and TSN focus on supervised learning for labeled samples from the source domain ($X_s$) and adversarial discriminative learning for unlabeled samples from the target domain ($X_t$), separately. More importantly, SN and TSN share the weights that are sequentially learned from both labeled and unlabeled samples. This technique is adopted in unsupervised domain adaptation to reduce the number of learnable parameters. The labeled samples enable a neural network to learn accurate segmentation predictions while the unlabeled ones bring unsupervised learning and further present a type of perturbation to regularize the model training. Furthermore, TTN conducts the weight self-ensembling part with replicating the average weights of the TSN instead of predictions. TTN solely takes unlabeled target images as input and then the mean square difference between TSN and TTN is computed for the same target sample. Different data augmentations (e.g., adding Gaussian noise and random intensity or brightness scaling) are applied to TSN and TTN to avoid loss vanishing issue. Basically, the U-Net with encoder-decoder structure is employed as the backbone of each network. Since U-Net is one of the most successful segmentation frameworks in medical imaging, the results can easily be generalized to other medical image analysis tasks.

For the CADA framework, a multi-scale input layer is extended to further enhance the feature interaction between the encoder and the decoder. Correspondingly, each scale input provides original image information to an encoder layer, which is followed by a decoder layer at the same network "pyramid" level. The rich original pixel-wise feature can infuse the interaction between encoder and decoder at the different feature-learning levels in the network. This infusion triggered by the multi-scale input can further guide the model learning and promote performance. To further investigate the capability of the CADA method, multiple discriminators are utilized in the decoder layers instead of a single one at the end of the network. These multiple discriminators encourage the encoder to learn the domain-invariant features consistently. More importantly, they can collaboratively distinguish the robust latent features, thus leading to a reliable and scalable domain adaptation framework.

Accordingly, in FIG. 2B, multi-scale inputs and outputs are utilized to adapt various levels of features hierarchically. During training, at each iteration, the source images are fed into the Source domain Network (SN) to generate the Source encoder Feature (SF) $P_{sf}$ and source decoder output $P_{so}$. Then, the source domain segmentation loss is obtained by comparing the $P_{so}$ with the source domain ground truth. The target domain student network (TSN) shares the same weights with the SN, and the weights of the Target domain Teacher Network (TTN) are the Exponential Moving Average (EMA) of the weights of the TSN. Adversarial losses for domain confusion are added for both encoder and decoder outputs of the SN and TSN. Moreover, MSE losses are added for both encoder and decoder outputs of TSN and TTN. To reduce the difficulty of high-dimensional feature calculations, the output of all encoders are compressed to one feature map output via a 1×1 convolutional layer. Discriminators can be added between all the intermediate decoder layers of SN and TSN. However, in the figure, the discriminators are shown to be added among the input ($P_{sf}$ and $P_{tsf}$) and output ($P_{so}$ and $P_{tso}$) of the decoders for simplicity.

In FIG. 2A and FIG. 2B, two discriminators are shown as being applied at the encoder and decoder of the networks, separately, to achieve adversarial discriminative learning. Two adversarial loss functions are calculated between SN and TSN. Each of the loss calculations is performed by two steps in each training iteration: (1) train a target domain segmentation network to maximize the adversarial loss $\mathcal{L}_{adv}$, thereby fooling the domain discriminator D to maximize the probability of the source domain feature $P_s$ being classified as target features:

$$\mathcal{L}_{adv}(X_s) = \mathbb{E}_{x_s \sim X_s} \log(1 - D(P_s)), \quad (1)$$

and (2) minimize the discriminator loss $\mathcal{L}_D$:

$$\mathcal{L}_d(X_s, X_t) = \mathbb{E}_{x_t \sim X_t} \log(D(P_t)) + \mathbb{E}_{x_s \sim X_s} \log(1 - D(P_s)), \quad (2)$$

where $P_t$ is the target domain feature.

Note that, in FIG. 2B, discriminators can be added between all the intermediate decoder layers of SN and TSN. However, in the figure, the discriminators are only added among the input ($P_{sf}$ and $P_{tsf}$) and output ($P_{so}$ and $P_{tso}$) of the decoders for simplicity.

In self-ensembling for domain adaptation of the systems of FIGS. 2A-2B, the training of the student model is iteratively improved by the task-specific loss, a moving average (EMA) model (teacher) of the student model, which can be illustrated as:

$$\phi'_t = \alpha \phi'_{t-1} + (1 - \alpha) \phi_t \quad (3)$$

where $\phi_t$ and $\phi'_t$ denote the parameters of the student network and the teacher network, respectively. EMA transfers a smooth version of the weights of the student to the teacher network. Thus, the teacher network performs more stable and robust than the student.

More specifically, at each iteration, a mini-batch of labeled source domain samples and unlabeled target samples are drawn from the target domain T. Then, the EMA predictions and the base predictions are generated by the teacher model and the student model respectively with different augmentation applied to the target samples. Afterward, a mean-squared error (MSE) loss between the EMA and target predictions is calculated. Finally, the MSE loss together with the task-specific loss on the labeled source domain data is minimized to update the parameters of the student network. Since the teacher model is an improved model at each iteration, the MSE loss helps the student model to learn from the unlabeled target domain images. Therefore, the student model and teacher model can work collaboratively to achieve robust and accurate predictions.

Unlike pre-existing systems and methods, exemplary systems and methods of the present disclosure appropriately integrate adversarial domain confusion and self-ensembling with an encoder-decoder architecture. In particular, adversarial domain confusion is applied to both the encoded features and decoded predictions between source domain network (SN) and target domain student network (TSN) to reduce the distribution differences. According to Equation 1 and Equation 2, this corresponds to the adversarial loss function $\mathcal{L}_{adv}^E$ for the encoder output of SN and TSN, and the adversarial loss function $\mathcal{L}_{adv}^D$ for the decoder output of SN and TSN:

$$\mathcal{L}_{adv}{}^{E}(X_s)=\mathbb{E}_{x_s\sim X_s}\log(1-D_E(P_{sf})), \quad (4)$$

$$\mathcal{L}_{adv}{}^{D}(X_s)=\mathbb{E}_{x_s\sim X_s}\log(1-D_D(P_{so})), \quad (5)$$

where $P_{sf}\in\mathbb{R}^{W_e\times H_e\times C_e}$ is the encoder output and $P_{so}\in\mathbb{R}^{W_d\times H_d\times C_d}$ is the decoder output. $H_d$ and $W_d$ are the width and height of the decoders' output; $C_d$ refers to pixel categories of the segmentation result, which is three in our cases. $H_e$, $W_e$, and $C_e$ are the width, height, channel of the encoders' output. $D_E$ and $D_D$ are the discriminator networks for the encoder and decoder outputs, respectively.

The discriminator loss $\mathcal{L}_d^E$ for the encoder feature and the discriminator loss $\mathcal{L}_d^D$ for decoder feature are as follows:

$$\mathcal{L}_d{}^{E}(X_s,X_t)=\mathbb{E}_{x_t\sim X_t}\log(D_E(P_{tsf}))+\mathbb{E}_{x_s\sim X_s}\log(1-D_E(P_{sf})), \quad (6)$$

$$\mathcal{L}_d{}^{D}(X_s,X_t)=\mathbb{E}_{x_t\sim X_t}\log(D_D(P_{tso}))+\mathbb{E}_{x_s\sim X_s}\log(1-D_D(P_{so})), \quad (7)$$

where $P_{tsf}\in\mathbb{R}^{W_e\times H_e\times C_e}$ is the encoder output and $P_{tso}\in\mathbb{R}^{W_d\times H_d\times C_d}$ is the decoder output of TSN.

Self-ensembling is also applied to both the encoded features and decoded predictions between the TSN and the target domain teacher network (TTN). In the present disclosure, MSE is used for the self-ensembling. The MSE loss $\mathcal{L}_{mse}^E$ between encoder outputs of TSN and TTN, and the MSE loss $\mathcal{L}_{mse}^D$ between decoder outputs of TSN and TTN can be formulated as:

$$\mathcal{L}_{mse}^E(X_t)=\mathbb{E}_{x_t\sim X_t}\left[\frac{1}{M}\sum_{i=1}^{M}(p_i^{tsf}-p_i^{ttf})^2\right], \quad (8)$$

$$\mathcal{L}_{mse}^D(X_t)=\mathbb{E}_{x_t\sim X_t}\left[\frac{1}{N}\sum_{i=1}^{N}(p_i^{tso}-p_i^{tto})^2\right]. \quad (9)$$

where $p_i^{tsf}$, $p_i^{ttf}$, $p_i^{tso}$, and $p_i^{tto}$ denote the $i^{th}$ element of the flattened predictions ($P_{tsf}$, $P_{ttf}$, $P_{tso}$, and $P_{tto}$) of the student encoder, student decoder, teacher encoder, teacher decoder, respectively. M and N are the number of elements in the encoder feature and decoder output, respectively.

In FIG. 2A, the same spatial-challenging augmentation $g(x, \phi)$ is used for both the teacher and student at each iteration with $g(x, \phi)$ applied to the training sample of the student and $g(x, \phi)$ applied to the predictions of the teacher, where $\phi$ is the transformation parameter. Dice loss is used as the segmentation loss for labeled images from the source domain. However, in FIG. 2B, cross-entropy is used as the segmentation loss for labeled images from the source domain. For FIGS. 2A-2B, Equations 4, 5, 6, 7, 8, and 9 are combined to obtain the total loss, which can be formulated as shown below.

$$\mathcal{L}_{total}(X_s,X_t)=\mathcal{L}_{seg}(X_s)+\lambda_{adv}^E\mathcal{L}_d^E(X_s,X_t)+\lambda_{adv}^D\mathcal{L}_d^D(X_s,X_t)+\lambda_{mse}^E\mathcal{L}_{mse}^E(X_t)+\lambda_{mse}^D\mathcal{L}_{mse}^D(X_t), \quad (10)$$

where $\lambda_{adv}^E$, $\lambda_{adv}^D$, $\lambda_{mse}^E$, and $\lambda_{mse}^D$ balance the weights of the losses. They are cross-validated in our experiments. $\mathcal{L}_{seg}(X_s)$ is the segmentation loss. Based on Equation 10, we optimize the following min-max problem:

$$\min_{f_\phi,f_{\dot\phi}}\max_{D_E,D_D}\mathcal{L}_{total}(X_s,X_t), \quad (11)$$

where $f_\phi$ and $f_{\dot\phi}$ are the source domain network with trainable weight $\phi$ and target domain network with trainable weight $\dot\phi$. An exemplary training procedure is summarized in Algorithm 1 of FIGS. 2C-2D.

For the model frameworks of FIGS. 2A and 2B, extensive experiments have been conducted on the REFUGE dataset to validate the effectiveness of the exemplary methods of the present disclosure. The dataset included 400 source domain retinal fundus images (supervised training dataset) with size 2124×2056, acquired by a Zeiss Visucam 500 camera, 400 labeled (testing dataset) and 400 additional unlabeled (unsupervised training dataset) target domain retinal fundus images with size 1634×1634 collected by a Canon CR-2 camera. As different cameras were used, the source and target domain images had totally distinct appearances (e.g., color and texture). The optic disc and optical cup regions were carefully delineated by the experts. All of the methods in this section were supervised by the annotations of the source domain and evaluated by the disc and cup dice indices (DI), and the cup-to-disc ratio (CDR) on the target domain.

For data preprocessing, in each case, the center of the optic disc was detected by pre-trained disc-aware ensemble network, and then optic disc regions were centered and cropped with a size of 600×600 for supervised training dataset and 500×500 for unsupervised training dataset and test dataset. This was due to the different sizes of images acquired by the two cameras. During training, all images were resized to a small size of 128×128 in order to adapt the network's receptive field. For training, the U-Net was used for both the student and the teacher network. All experiments were processed on either Python v2.7 or Python v3.6, and PyTorch 1.0.0 with GEFORCE GTX TITAN GPUs.

Figure 3:
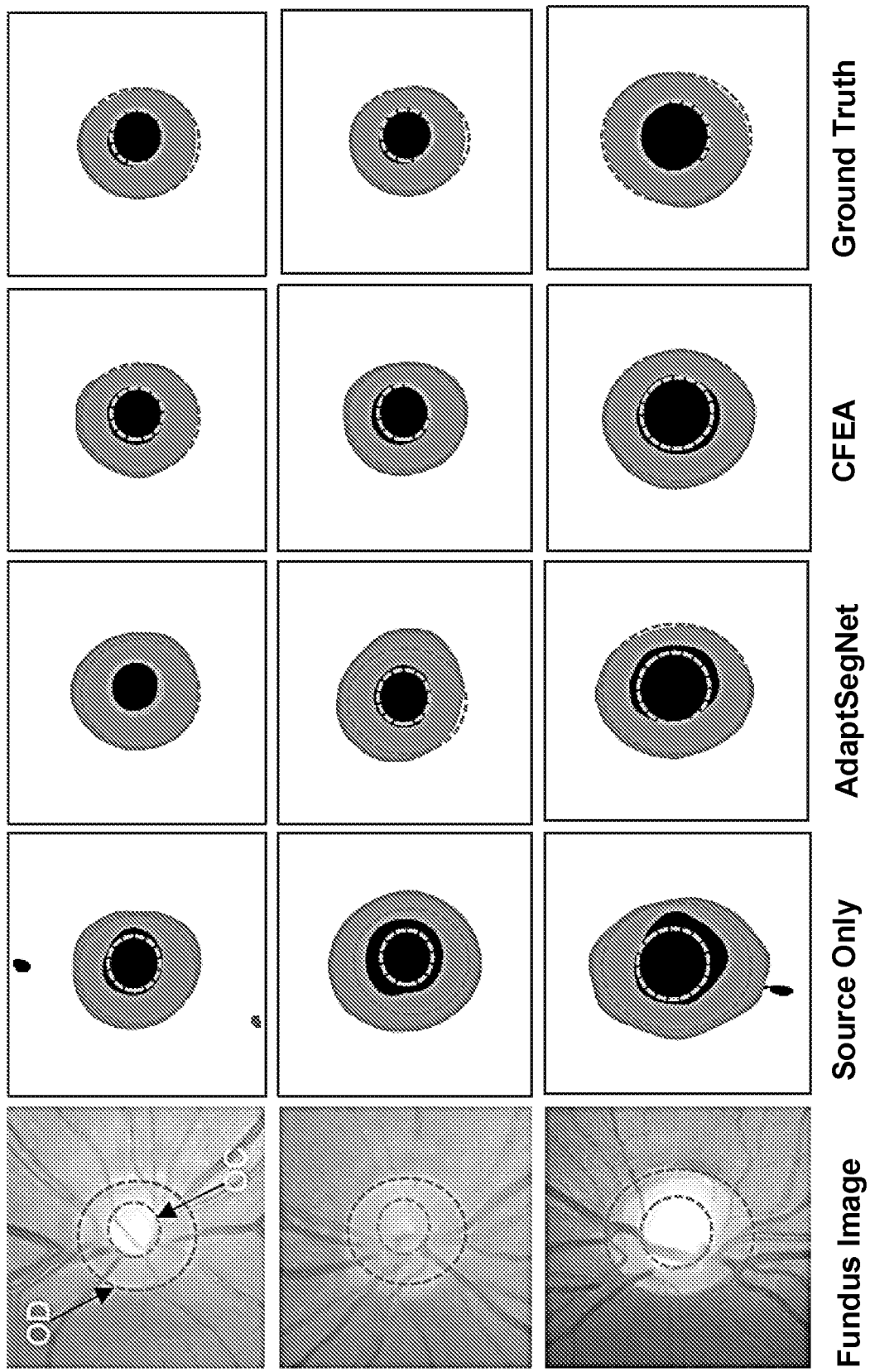
FIG. 3 shows visual examples of optic disc and cup segmentation by a model trained with pre-existing methods, an exemplary CFEA adaptation framework, and an exemplary CADA adaptation framework in accordance with various embodiments of the present disclosure.

The CFEA and the CADA models were trained on the source domain data acquired by the Zeiss Visucam 500 camera in a supervised manner and on the target domain data acquired by the Canon CR-2 camera in an unsupervised manner, simultaneously. The fully trained segmentation network was then evaluated on the test dataset, which included 400 retinal fundus images acquired by the Canon CR-2 camera. To demonstrate a particular method's effectiveness, the segmentation network was trained on source domain data only in a supervised manner and then was tested on the test data. In addition, a baseline-AdaptSegNet was trained in the same way as the segmentation networks of FIGS. 2A-2B. AdaptSegNet represents one of the state-of-the-art unsupervised domain adaptation methods for image segmentation, which also supplies adversarial learning for domain adaptation. The main results are shown in Table 1 (below) and FIG. 3 shows the visual examples of the optic disk and cup segmentation, where the black and gray regions denote the cup and disc segmentations, respectively. From the left to right, the figure shows a fundus image, the model trained on source data only, the baseline (AdaptSegNet) model, the model trained with an exemplary CFEA adaptation framework, the model trained with an exemplary CADA adaptation framework, and ground truth.

In particular, Table 1 shows the results of adapting a source domain to a target domain. As discussed, the exemplary methods were evaluated on 400 test images. Three metrics were used to evaluate a model's performance, the mean Dice coefficient for the optic cups, the mean Dice coefficient for the optic disc, and the mean absolute error for the vertical cup to disc ratio (CDR), in which the larger value for OD and OC means better segmentation results and, for CDR, the smaller value represents better results. "Source only" means the model only trained on source domain in a supervised manner.

From the table, the model trained on source data completely fails for target data, and the baseline can have satisfactory results on target data. By comparing the exemplary models for CFEA and CADA with the baseline, as one can see, the CFEA and CADA models outperform the state-of-the-art method consistently for OD, OC, and CDR. These results indicate that each of the CFEA and CADA frameworks has a capability of overcoming domain shifts, thus allowing us to build a robust and accurate model.

TABLE 1

| Evaluation-Index | Source Only | AdaptSegNet | CFEA | CADA |
|---|---|---|---|---|
| Optic Cup | 0.7317 | 0.8198 | 0.8627 | 0.8714 |
| Optic Disk | 0.8532 | 0.9315 | 0.9416 | 0.9498 |
| CDR | 0.0676 | 0.0588 | 0.0481 | 0.0447 |

Figure 4A:
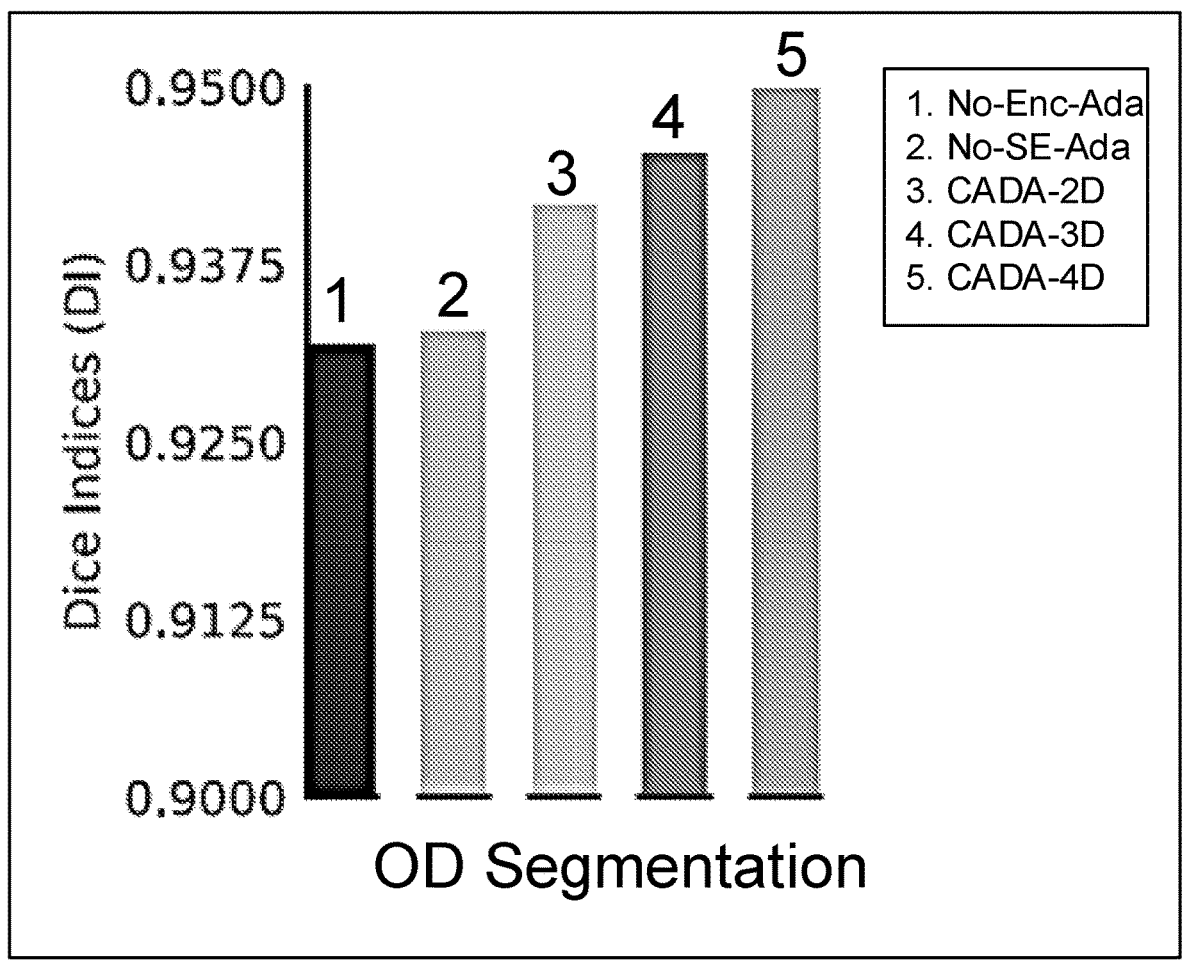
FIGS. 4A-4C shows a performance comparison of models under an ablation study by making various modifications to the CADA adaptation framework in accordance with the present disclosure.
Figure 4B:
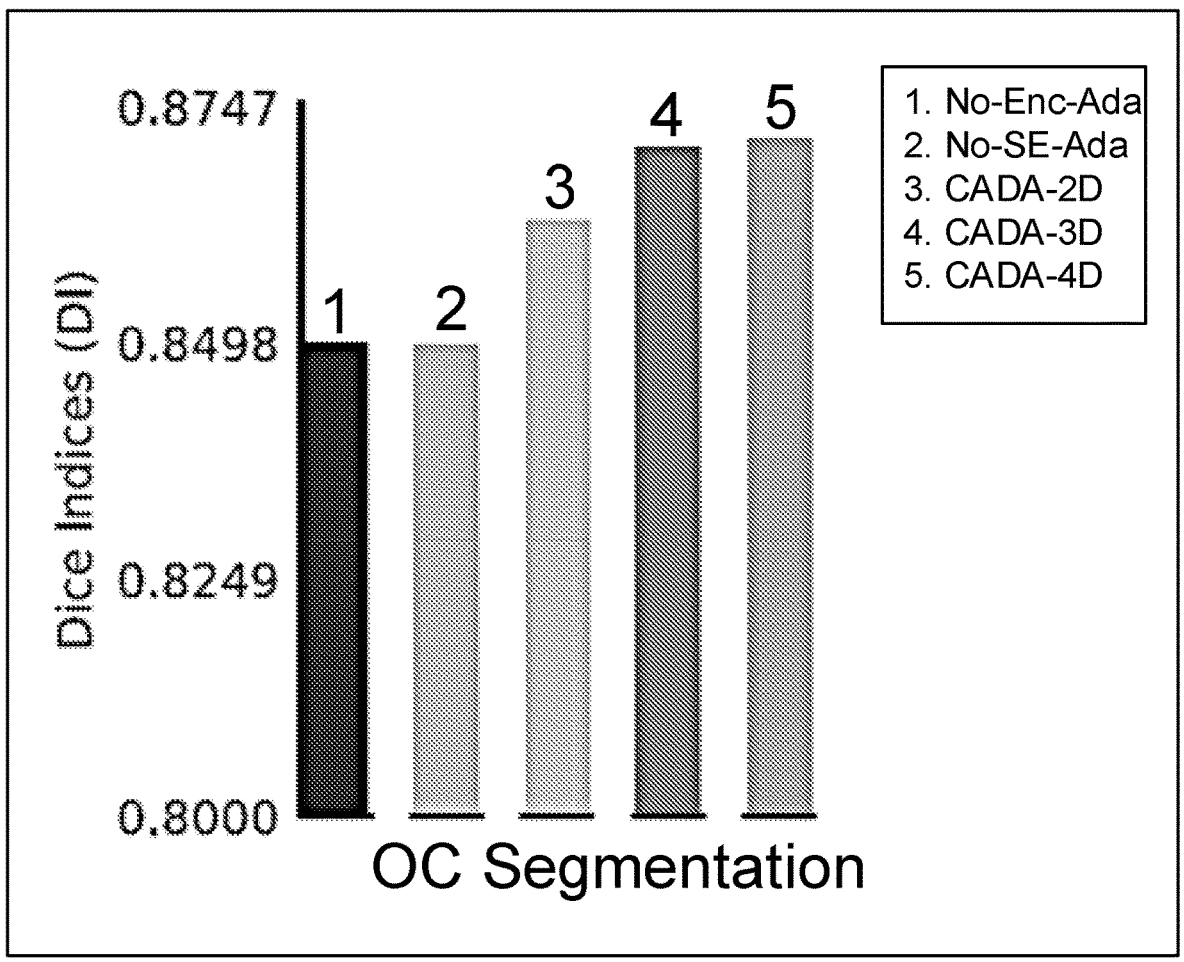
Figure 4C:
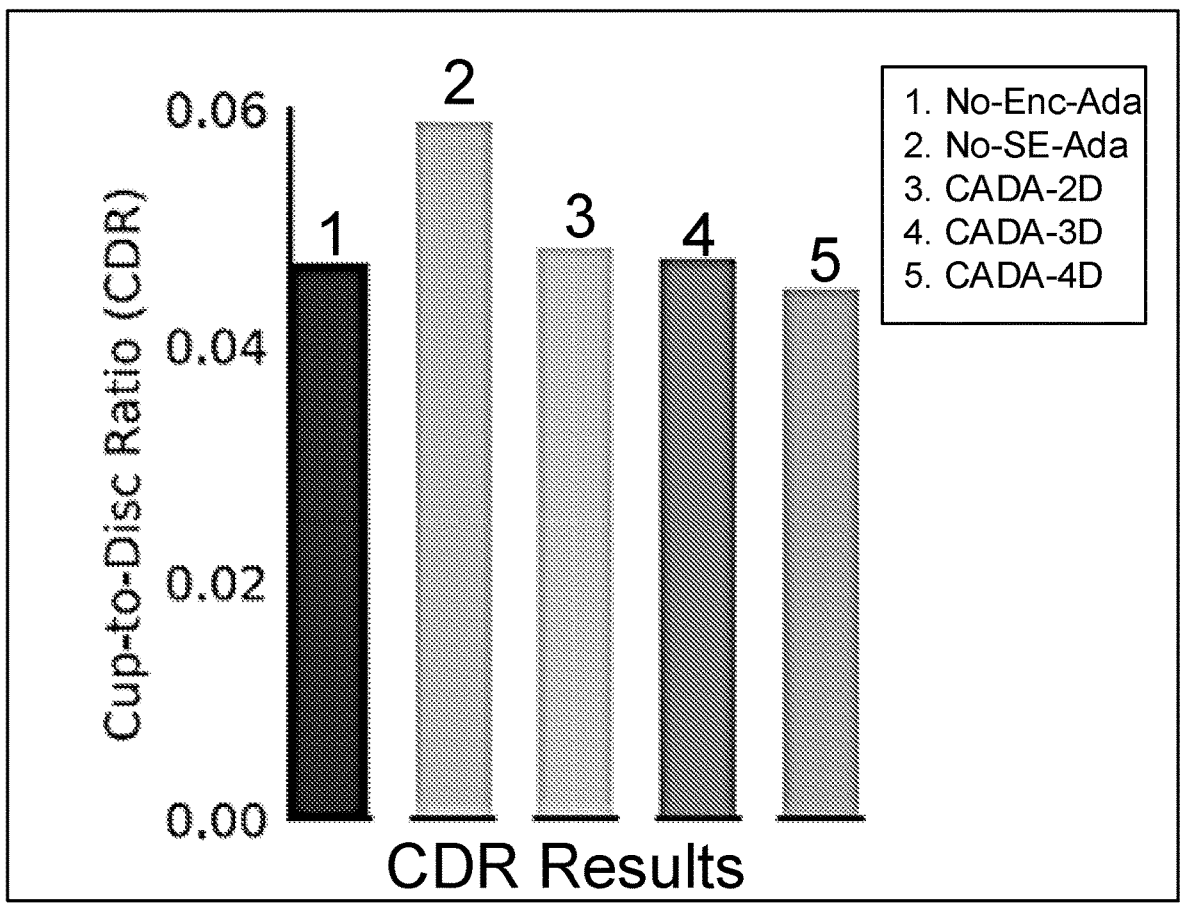

For the CADA framework (FIG. 2B) in order to demonstrate the importance of encoder adaptation modules, the adversarial discriminator $D_E$ and the MSE module $mse_E$ were removed from the encoders and then the model was retrained. FIGS. 4A-4C show the performance comparison of the models with modifications on the test dataset under an ablation study to investigate the effectiveness of the CADA framework. In particular, the ablation study investigates the importance of the encoder adversarial discriminative adaptation, the power of weights self-ensembling adaptation, the scalability of using multiple discriminators adaptation, and the choice of the various combinations of the weights of loss functions. As one can see, without the encoder adaptation, the performance drops apparently. This comparison result may indicate that the encoder discriminative adaptation module is a crucial component for learning the domain-invariant representation.

To investigate how self-ensembling adaptation affected the domain adaptation performance, an exemplary CADA framework was retrained after removing the teacher network. The performance comparison of the models with modifications is shown in FIGS. 4A-4C. In the figures, No-Enc-Ada means removing the discriminator from the encoder and only applying a discriminator on the decoder. No-SE-Ada means removing self-ensembling (the teacher network) from the CADA. It is noted that CADA-2D, CADA-3D, and CADA-4D represent applying two, three, and four discriminators to the decoder layers, separately, in which all CADA models have one discriminator at the end of encoder. Notably, CADA-2D is the method utilized in a CFEA embodiment.

As one can see, the average performance on the test dataset is much worse than using both adversarial domain confusion and self-ensembling adaptation. Especially, for predicting CDR, in FIG. 4C, we can see that without weights ensembling, the CDR prediction drops down significantly. This comparison result shows that self-ensembling can significantly improve the model's robustness and the generalizability for the domain shift. More importantly, weight ensembling can reduce the model uncertainty of learning domain-invariant latent features when incorporating multiple discriminators in a different feature learning space. Meanwhile, weight assembling is able to enforce all discriminators to maximize their ability to discriminate the deeper latent space features.

For a multiple discriminators adaptation study (CADA-2,3,4D), multiple discriminators at the decoder were exploited to further investigate the maximum power of collaborative feature learning and to compare the results of applying different numbers of discriminators to different decoder layers. As one can see with CADA-2D, CADA-3D, and CADA-4D in FIGS. 4A-4C, with the more discriminators used, a better result is able to be obtained. When discriminators were applied to all decoder layers (e.g., one is at the end of the encoder and another four are at each layer of the decoder), the best result was obtained. More importantly, the results of this comparison further indicates that collaborative feature learning between adversarial adaptation and dynamic weight ensembling can overcome a domain shift.

Figure 5:
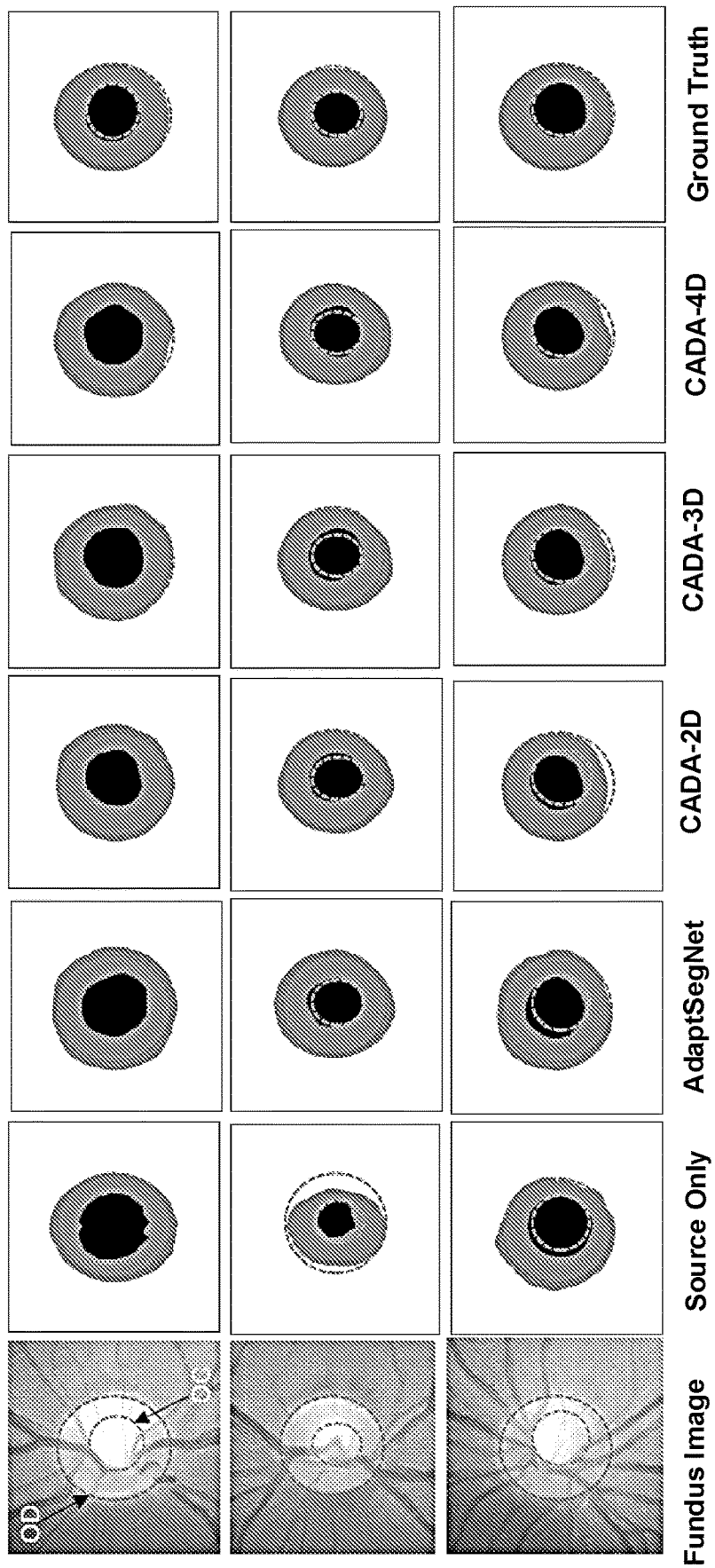
FIG. 5 shows visual examples of optic disc and cup segmentation by a model trained with pre-existing methods and an exemplary CADA adaptation framework having two discriminators at the decoder (CADA-2D), having three discriminators at the decoder layer (CADA-3D), and having four discriminators at the decoder layer (CADA-4D) in accordance with various embodiments of the present disclosure.

The various combinations of λ for balancing the segmentation, adversarial, and self-ensembling loss have also been evaluated. Due to the multiple possible combinations, it is impossible to study all of them. Thus, pre-existing studies and cross-validation have been used to investigate the most effective λ combinations, in which the following combination was found to be the most effective one that can stabilize an exemplary CADA framework training: $\lambda_{seg}=1$, $\lambda_{adv}^E=0.002$, $\lambda_{adv}^D=0.018$, $\lambda_{mse}^E=0.057$, $\lambda_{mse}^D=0.079$. As such, FIG. 5 shows the qualitative results demonstrating the effectiveness of the exemplary domain adaptation model. In particular, FIG. 5 provides qualitative examples of the optic disc and cup segmentation, where the black and gray regions denote the cup and disc segmentation, respectively. From the left to right, the figure shows the fundus image, the model trained on source data only, the baseline (AdaptSegNet), the model trained with an exemplary CADA domain adaptation framework having two discriminators at the decoder (CADA-2D), the model trained with an exemplary CADA domain adaptation framework having three discriminators at the decoder (CADA-3D), the model trained with an exemplary CADA domain adaptation framework having four discriminators at the decoder (CADA-4D), and ground truth. As one can see, these qualitative results are consistent with FIGS. 4A-4C and can further support that collaboration between adversarial learning and dynamic weight ensembling is an effective strategy to overcome a domain shift in fundus images.

In accordance with the present disclosure, a novel CFEA system/method and a novel CADA system/method are presented for unsupervised domain adaptation. An exemplary CFEA framework or CADA framework collaboratively combines adversarial discriminative learning and self-ensembling to obtain domain-invariant features from both feature representation (encoder) and output space (decoder). For CADA, multi-scale inputs provide hierarchical features to the collaborative learning process, in one embodiment. For either CFEA or CADA, self-ensembling can stabilize the adversarial learning and prevent the network from getting stuck in a sub-optimal solution, in various embodiments. From a complementary perspective, adversarial learning can consistently provide various model space and time-dependent weights to self-ensembling, which can accelerate the learning of the domain invariant features and further enhance the stabilization of adversarial learning, forming a benign collaborative circulation and unified framework. Moreover, in CADA, multiple discriminators can be applied to the multi-scale output from each layer of the decoder. These adversarial discriminative modules collaboratively encourage the encoder to extract the latent domain-invariant features. In CFEA, the collaborative mutual benefits from both adversarial feature learning and ensembling weights during an end-to-end learning process lead to a robust and accurate model. Further, in CADA, the collaborative mutual benefits from multi-scale inputs, adversarial discriminative feature learning, weights self-ensembling, and multi-scale outputs during an end-to-end learning process, likewise result in a robust and accurate model.

Notably, an exemplary CADA framework can be generalized to represent learning on large-scale unlabeled data. For example, a discriminator applied to the encoder can be easily replaced by one contrastive loss function, in which the encoder can learn the rich representations rather than the invariant features. Then, in one embodiment, the encoder can be fine-tuned with limited labeled data for specific tasks, such as image classification and segmentation. For CADA, adversarial discriminative learning can be applied in two phases of the network, i.e., intermediate representation space and output space, thereby intensifying feature adaptation. For both CFEA and CADA, simultaneously transferring weights with EMA from both the encoder and the decoder during model training is a significant novelty compared to pre-existing representation learning methods.

In terms of the running time, the CFEA and CADA frameworks need relatively higher computational costs during the training stage to help the segmentation network to adapt to the target domain. However, in the testing stage, the computational costs are the same as a standard U-Net network, as the images only need to go through the TTN network. Experimental results demonstrate the superiority of an exemplary CFEA and CADA framework over the state-of-the-art method with a significant performance gain. The CFEA and CADA approaches are general and can be easily extended to other semi-supervised and unsupervised representation learning problems.

CFEA and CADA are interactive paradigms which present an exquisite collaborative adaptation through both adversarial learning and ensembling weights. In particular, in order to produce a better prediction for the unlabeled target domain data, domain-invariance and model generalizability are simultaneously achieved via employing adversarial learning and maintaining an exponential moving average (EMA) of the historical weights during training. In particular, domain-invariance is simultaneously achieved with maintaining an exponential moving average of the historical predictions, which provides a better prediction for the unlabeled data, via ensembling weights during training. Without annotating any sample from the target domain, multiple adversarial losses in encoder and decoder layers guide the extraction of domain-invariant features to confuse the domain classifier and meanwhile aid the ensembling of smoothing weights. Meanwhile, the ensembling of weights via EMA reduces the uncertainty of adapting multiple discriminator learning. Comprehensive experimental results demonstrate that the CFEA and CADA models can overcome performance degradation to a domain shift and outperform the state-of-the-art methods in segmenting retinal optic disc and cup from fundus images with a significant performance gain.

Figure 6:
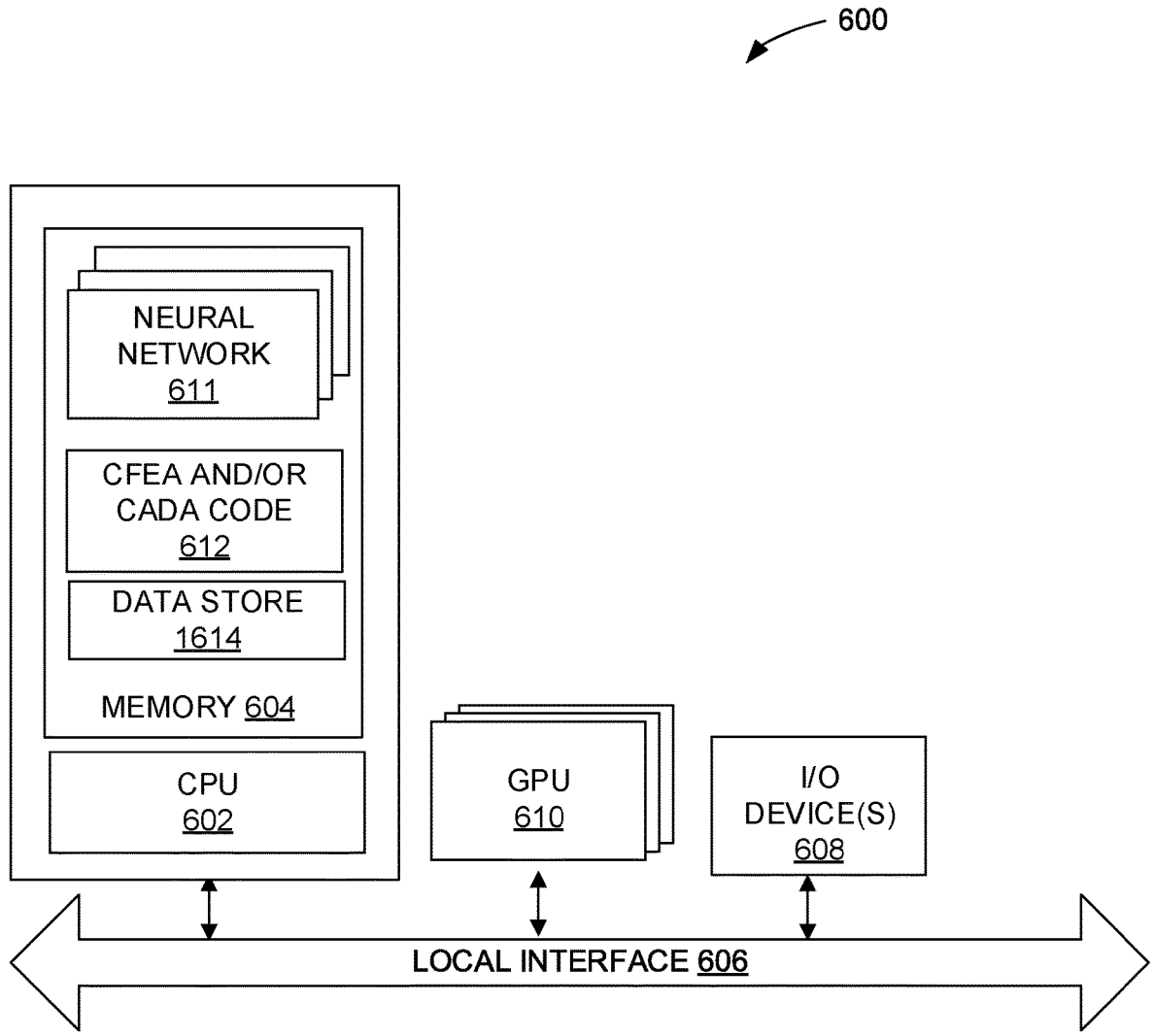
FIG. 6 shows a schematic block diagram of a computing device that can be used to implement various embodiments of the present disclosure.

FIG. 6 depicts a schematic block diagram of a computing device 600 that can be used to implement various embodiments of the present disclosure. An exemplary computing device 600 includes at least one processor circuit, for example, having a processor 602 and a memory 604, both of which are coupled to a local interface 606, and one or more input and output (I/O) devices 608. The local interface 606 may comprise, for example, a data bus with an accompanying address/control bus or other bus structure as can be appreciated. The computing device 600 further includes Graphical Processing Unit(s) (GPU) 610 that are coupled to the local interface 606 and may utilize memory 604 and/or may have its own dedicated memory. The CPU and/or GPU(s) can perform various operations such as image enhancement, graphics rendering, image/video processing, recognition (e.g., text recognition, object recognition, feature recognition, etc.), image stabilization, machine learning, filtering, image classification, and any of the various operations described herein.

Stored in the memory 604 are both data and several components that are executable by the processor 602. In particular, stored in the memory 604 and executable by the processor 602 are code for implementing one or more neural networks (e.g., convolutional neural network (CNN)) models 611 and logic/instructions 612 for training the neural network model(s) 611 using an exemplary unsupervised domain adaptation framework (e.g., CFEA and/or CADA). Also stored in the memory 604 may be a data store 614 and other data. The data store 614 can include an image database for source images, target images, and potentially other data. In addition, an operating system may be stored in the memory 604 and executable by the processor 602. The I/O devices 608 may include input devices, for example but not limited to, a keyboard, mouse, etc. Furthermore, the I/O devices 608 may also include output devices, for example but not limited to, a printer, display, etc.

Certain embodiments of the present disclosure can be implemented in hardware, software, firmware, or a combination thereof. If implemented in software, the CFEA and/or CADA logic or functionality are implemented in software or firmware that is stored in a memory and that is executed by a suitable instruction execution system. If implemented in hardware, the CFEA and/or CADA logic or functionality can be implemented with any or a combination of the following technologies, which are all well known in the art: discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Therefore, at least the following is claimed:

1. A method for training a neural network for ocular cup (OC) or ocular disc (OD) detection, the method comprising:
    for a plurality of training iterations, drawing a mini-batch of labeled source domain samples from a source domain and unlabeled target samples from a target domain, wherein a domain shift exists between the source domain and the target domain;
    initiating training of a first network to learn detection of OC or OD regions within a labeled source sample from the source domain, wherein training weights of the first network are adapted based on a loss calculated from an output of the first network and a ground truth for a same source sample;
    sharing training weights of the first network with a second network;
    initiating training of the second network to learn detection of OC or OD regions within an unlabeled sample from the target domain, wherein training weights of the second network are adapted based on an adversarial loss calculated from an output of the second network and the output of the first network for the same sample across the source and target domains;

adjusting the training weights of the first network and the second network based on the calculated adversarial loss;

transferring average training weights of the second network to a third network;

initiating training of the third network to learn detection of OC and OD regions within an unlabeled sample from the target domain;

computing a mean square error loss between an output of the third network and the output of the second network for a same target sample;

adjusting the training weights of the second network based on the mean square error loss computation; and proceeding with a next iteration of the plurality of training iterations.

2. The method of claim 1, wherein the target and source domains comprise retinal fundal images.

3. The method of claim 2, wherein the target domain of retinal fundal images is captured from a first retinal fundal camera and the source domain of retinal fundal images is captured from a second retinal fundal camera that is different model camera than the first retinal fundal camera.

4. The method of claim 1, wherein the first, second, and third networks comprise encoder decoder convolutional networks.

5. The method of claim 4, wherein adversarial losses for domain confusion are added for both encoder and decoder outputs of the first network and the second network.

6. The method of claim 4, wherein the first, second, and third networks feature multiple discriminators in a plurality of decoder layers.

7. The method of claim 6, wherein the multiple discriminators comprise 3 or more discriminators.

8. The method of claim 1, wherein the second network comprises a multi-scale input layer, wherein each scale input provides original image information to an encoder layer.

9. The method of claim 1, wherein the training weights of the third network are an exponential moving average of the training weights of the second network.

10. The method of claim 1, further comprising determining, by the third network after completion of training, a Cup to Disc Ratio for a retinal fundal image.

11. A system comprising:
one or more processors; and
memory storing computer-executable instructions that, when executed by the one or more processors, cause performance of operations comprising:
for a plurality of training iterations, drawing a mini-batch of labeled source domain samples from a source domain and unlabeled target samples from a target domain, wherein a domain shift exists between the source domain and the target domain;
initiating training of a first network to learn detection of OC or OD regions within a labeled source sample from the source domain, wherein training weights of the first network are adapted based on a loss calculated from an output of the first network and a ground truth for a same source sample;
sharing training weights of the first network with a second network;
initiating training of the second network to learn detection of OC or OD regions within an unlabeled sample from the target domain, wherein training weights of the second network are adapted based on an adversarial loss calculated from an output of the second network and the output of the first network for the same sample across the source and target domains;
adjusting the training weights of the first network and the second network based on the calculated adversarial loss;
transferring average training weights of the second network to a third network;
initiating training of the third network to learn detection of OC and OD regions within an unlabeled sample from the target domain;
computing a mean square error loss between an output of the third network and the output of the second network for a same target sample;
adjusting the training weights of the second network based on the mean square error loss computation; and
proceeding with a next iteration of the plurality of training iterations until each iteration of the plurality of training iterations has been completed.

12. The system of claim 11, wherein the target and source domains comprise retinal fundal images.

13. The system of claim 12, wherein the target domain of retinal fundal images is from a first retinal fundal camera and the source domain of retinal fundal images is from a second retinal fundal camera that is different model camera than the first retinal fundal camera.

14. The system of claim 13, wherein each of the first network, the second network, and the third network comprise an encoder decoder convolutional network.

15. The system of claim 14, wherein adversarial losses for domain confusion are added for both encoder and decoder outputs of the first network and the second network.

16. The system of claim 14, wherein the first, second, and third networks feature multiple discriminators in a plurality of decoder layers.

17. The system of claim 16, wherein the multiple discriminators comprise 3 or more discriminators.

18. The system of claim 11, wherein each of the first network, the second network, and the third network comprise a multi-scale input layer, wherein each scale input provides original image information to an encoder layer.

19. The system of claim 11, wherein the training weights of the third network are an exponential moving average of the training weights of the second network.

20. The system of claim 11, wherein the operations further comprise determining, by the third network after completion of training, a Cup to Disc Ratio for a retinal fundal image.

* * * * *